United States Patent [19]

Ayer

[11] 4,200,740
[45] Apr. 29, 1980

[54] 2-DECARBOXY-2-HYDROXYMETHYL-TRANS-4,5-DIDEHYDRO-PGI$_1$ COMPOUNDS

[75] Inventor: Donald E. Ayer, Kalamazoo, Mich.

[73] Assignee: The Upjohn Company, Kalamazoo, Mich.

[21] Appl. No.: 938,546

[22] Filed: Aug. 31, 1978

Related U.S. Application Data

[63] Continuation-in-part of Ser. No. 821,542, Aug. 3, 1977.

[51] Int. Cl.$^2$ .......................................... C07D 307/93
[52] U.S. Cl. .................................. 542/426; 542/429; 260/346.22

[58] Field of Search .................. 260/346.22; 542/426, 542/429

[56] References Cited

PUBLICATIONS

Corey et al., J.A.C.S./99:6/Mar. 1977, pp. 2006–2008.

*Primary Examiner*—Natalie Trousof
*Assistant Examiner*—Bernard Dentz
*Attorney, Agent, or Firm*—Robert A. Armitage

[57] ABSTRACT

The present invention relates to certain structural and pharmacological analogs of prostacyclin (PGI$_2$) which are 2-decarboxy-2-hydroxymethyl-trans-4,5-didehydro-PGI$_1$ compounds. These novel pharmacological agents are useful as smooth muscle stimulators.

82 Claims, No Drawings

2-DECARBOXY-2-HYDROXYMETHYL-TRANS-4,5-DIDEHYDRO-PGI₁ COMPOUNDS

CROSS REFERENCE TO RELATED APPLICATIONS

The present application is a continuation-in-part of Ser. No. 821,542, filed Aug. 3, 1977, now pending.

The present invention provides pharmacological agents, the preparation and use of which is described in U.S. Pat. No. 4,109,082, issued Aug. 22, 1978, the relevant portion of which is incorporated here by reference. These pharmacological agents are characterized by smooth muscle stimulatory action and are related structurally to prostacyclin, being 2-decarboxy-2-hydroxymethyl-trans-4,5-didehydro-PGI₁ compounds.

What is claimed is:

1. A prostacyclin analog of the formula

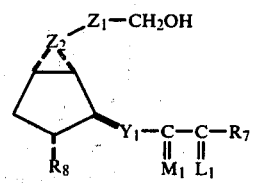

wherein $Y_1$ is trans—CH=CH—, cis—CH=CH—, or —CH₂CH₂—;
wherein $Z_2$ is

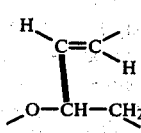 (1)

or

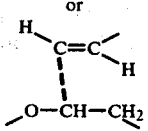 (2)

wherein $Z_1$ is
 (1) —(CH₂)$_g$—CH₂—CH₂—, or
 (2) —(CH₂)$_g$—CH₂—CF₂—,
  wherein g is the integer zero, one, or 2;
wherein $R_8$ is hydrogen, hydroxy, or hydroxymethyl;
wherein $M_1$ is

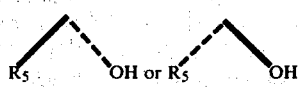

wherein $R_5$ is hydrogen or alkyl with one to 4 carbon atoms, inclusive; and
wherein $L_1$ is

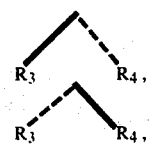

or a mixture of

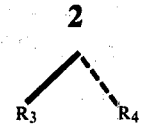

and

, wherein $R_3$ and $R_4$ are hydrogen, methyl, or fluoro, being the same or different, with the proviso that one of $R_3$ and $R_4$ is fluoro only when the other is hydrogen or fluoro; and
wherein $R_7$ is

 (1)

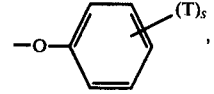 (2)

, or (3)

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl.

2. A prostacyclin analog according to claim 1, wherein $Y_1$ is trans—CH=CH—.

3. A prostacyclin analog according to claim 2, wherein $Z_2$ is a mixture of

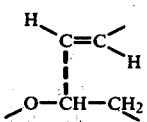 and 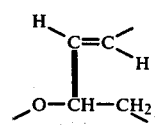

4. 2-Decarboxy-2-hydroxymethyl-(6RS)-trans-4,5-didehydro-PGI₁, a prostacyclin analog according to claim 3.

5. A prostacyclin analog according to claim 2, wherein $Z_2$ is

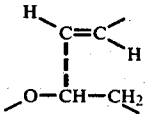

6. 2-Decarboxy-2-hydroxymethyl-trans-4,5-didehydro-6α-PGI₁, a prostacyclin analog according to claim 5.

7. 2-Decarboxy-2-hydroxymethyl-15-methyl-trans-4,5-didehydro-6α-PGI₂, a prostacyclin analog according to claim 5.

8. 2-Decarboxy-2-hydroxymethyl-16,16-dimethyl-trans-4,5-didehyro-6α-PGI₁, a prostacyclin analog according to claim 5.

9. 2-Decarboxy-2-hydroxymethyl-16,16-difluoro-trans-4,5-didehydro-6α-PGI₁, a prostacyclin analog according to claim 5.

10. A prostacyclin analog according to claim 2, wherein Z₂ is

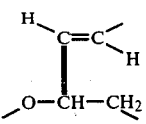

11. A prostacyclin analog according to claim 10, wherein Z₁ is —(CH₂)$_g$—CH₂—CF₂—.

12. 2-Decarboxy-2-hydroxymethyl-2,2-difluro-trans-4,5-didehydro-6β-PGI₁, a prostacyclin analog according to claim 11.

13. A prostacyclin analog according to claim 10, wherein Z₁ is —(CH₂)$_g$—CH₂—CH₂—.

14. A prostacyclin analog according to claim 13, wherein g is zero.

15. A prostacyclin analog according to claim 14, wherein R₇ is

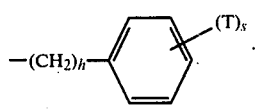

16. 2-Decarboxy-2-hydroxymethyl-17-phenyl-18,19,20-trinor-trans-4,5-didehydro-6β-PGI₁, a prostacyclin analog according to claim 15.

17. A prostacyclin analog according to claim 14, wherein R₇ is

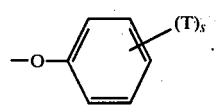

18. 2-Decarboxy-2-hydroxymethyl-16-phenoxy-17,18,19,20-tetranor-trans-4,5-didehydro-6β-PGI₁, a prostacyclin analog according to claim 17.

19. A prostacyclin analog according to claim 14, wherein R₇ is —(CH₂)$_m$—CH₃—.

20. A prostacyclin analog according to claim 19, wherein R₅ is methyl.

21. 2-Decarboxy-2-hydroxymethyl-15-methyl-trans-4,5-didehydro-6β-PGI₁, a prostacyclin analog according to claim 20.

22. A prostacyclin analog according to claim 19, wherein R₅ is hydrogen.

23. A prostacyclin analog according to claim 22, wherein at least one of R₃ and R₄ is fluoro.

24. 2-Decarboxy-2-hydroxymethyl-16,16-difluoro-trans-4,5-didehydro-6β-PGI₁, a prostacyclin analog according to claim 23.

25. A prostacyclin analog according to claim 22, wherein at least one of R₃ and R₄ is methyl.

26. 2-Decarboxy-2-hydroxymethyl-16,16-dimethyl-trans-4,5-didehydro-6β-PGI₁, a prostacyclin analog according to claim 25.

27. A prostacyclin analog according to claim 22, wherein R₃ and R₄ are both hydrogen.

28. 2-Decarboxy-2-hydroxymethyl-trans-4,5-didehydro-6β-PGI₁, a prostacyclin analog according to claim 27.

29. A prostacyclin analog according to claim 1, wherein Y₁ is cis—CH=CH—.

30. A prostacyclin analog according to claim 29, wherein Z₂ is a mixture of

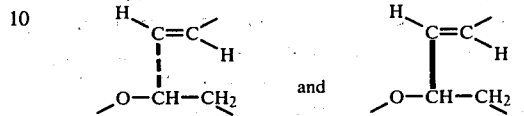

31. 2-Decarboxy-2-hydroxymethyl-6(RS)-trans-4,5-didehyro-cis-13-PGI₁, a prostacyclin analog according to claim 30.

32. A prostacyclin analog according to claim 29, wherein Z₂ is

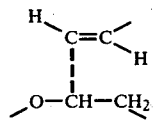

33. 2-Decarboxy-2-hydroxymethyl-trans-4,5-didehyro-cis-13-6α-PGI₁, a prostacyclin analog according to claim 32.

34. 2-Decarboxy-2-hydroxymethyl-15-methyl-trans-4,5-didehydro-cis-13-6α-PGI₁, a prostacyclin analog according to claim 32.

35. 2-Decarboxy-2-hydroxymethyl-16,16-dimethyl-trans-4,5-didehydro-cis-13-6α-PGI₁, a prostacyclin analog according to claim 32.

36. 2-Decarboxy-2-hydroxymethyl-16,16-difluoro-trans-4,5-didehydro-cis-13-6α-PGI₁, a prostacyclin analog according to claim 32.

37. A prostacyclin analog according to claim 29, wherein Z₂ is

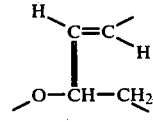

38. A prostacyclin analog according to claim 37, wherein Z₁ is —(CH₂)$_g$—CH₂—CF₂—.

39. 2-Decarboxy-2-hydroxymethyl-2,2-difluoro-trans-4,5-didehydro-cis-13-6β-PGI₁, a prostacyclin analog according to claim 38.

40. A prostacyclin analog according to claim 37, wherein Z₁ is —(CH₂)$_g$—CH₂—CH₂—.

41. A prostacyclin analog according to claim 40, wherein g is zero.

42. A prostacyclin analog according to claim 41, wherein R₇ is

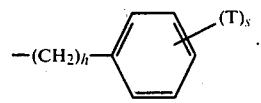

43. 2-Decarboxy-2-hydroxymethyl-17-phenyl-18,19,20-trinor-trans-4,5-didedydro-cis-13-6β-PGI₁, a prostacyclin analog according to claim 42.

44. A prostacyclin analog according to claim 41, wherein R₇ is

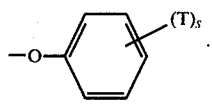

45. 2-Decarboxy-2-hydroxymethyl-16-phenoxy-17,18,19,20-tetranor-trans-4,5-didehydro-cis-13-6β-PGI₁, a prostacyclin analog according to claim 44.

46. A prostacyclin analog according to claim 41, wherein R₇ is —(CH₂)$_m$—CH₃—.

47. A prostacyclin analog according to claim 46, wherein R₅ is methyl.

48. 2-Decarboxy-2-hydroxymethyl-15-methyl-trans-4,5-didehydro-cis-13-6β-PGI₁, a prostacyclin analog according to claim 47.

49. A prostacyclin analog according to claim 46, wherein R₅ is hydrogen.

50. A prostacyclin analog according to claim 49, wherein at least one of R₃ and R₄ is fluoro.

51. 2-Decarboxy-2-hydroxymethyl-16,16-difluoro-trans-4,5-didehydro-cis-13-6β-PGI₁, a prostacyclin analog according to claim 50.

52. A prostacyclin analog according to claim 49, wherein at least one of R₃ and R₄ is methyl.

53. 2-Decarboxy-2-hydroxymethyl-16,16-dimethyl-trans-4,5-didehydro-cis-13-6β-PGI₁, a prostacyclin analog according to claim 52.

54. A prostacyclin analog according to claim 49, wherein R₃ and R₄ are both hydrogen.

55. 2-Decarboxy-2-hydroxymethyl-trans-4,5-didehydro-cis-13-6β-PGI₁, a prostacyclin analog according to claim 54.

56. A prostacyclin analog according to claim 1, wherein Y₁ is —CH₂CH₂—.

57. A prostacyclin analog according to claim 56, wherein Z₂ is a mixture of

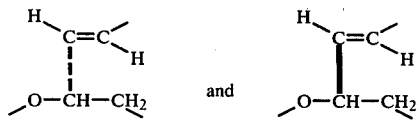

58. 2-Decarboxy-2-hydroxymethyl-6(RS)-trans-4,5-didehydro-13,-14-dihydro-PGI₁, a prostacyclin analog according to claim 57.

59. A prostacyclin analog according to claim 56, wherein Z₂ is

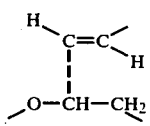

60. 2-Decarboxy-2-hydroxymethyl-trans-4,5-didehydro-13,14-dihydro-6α-PGI₁, a prostacyclin analog according to claim 59.

61. 2-Decarboxy-2-hydroxymethyl-15-methyl-trans-4,5-didehydro-13,14-dihydro-6α-PGI₁, a prostacyclin analog according to claim 59.

62. 2-Decarboxy-2-hydroxymethyl-16,16-dimethyl-trans-4,5-didehydro-13,14-dihydro-6α-PGI₁, a prostacyclin analog according to claim 59.

63. 2-Decarboxy-2-hydroxymethyl-16,16-difluoro-trans-4,5-didehydro-13,14-dihydro-6α-PGI₁, a prostacyclin analog according to claim 59.

64. A prostacyclin analog according to claim 56, wherein Z₂ is

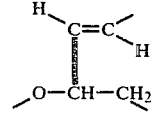

65. A prostacyclin analog according to claim 64, wherein Z₁ is —(CH₂)$_g$—CH₂-CF₂—.

66. 2-Decarboxy-2-hydroxymethyl-2,2-difluoro-trans-4,5-didehydro-13,-14-dihydro-6β-PGI₁, a prostacyclin analog according to claim 65.

67. A prostacyclin analog according to claim 64, wherein Z₁ is —(CH₂)$_g$—CH₂—CH₂—.

68. A prostacyclin analog according to claim 67, wherein g is zero.

69. A prostacyclin analog according to claim 68, wherein R₇ is

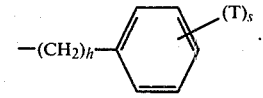

70. 2-Decarboxy-2-hydroxymethyl-17-phenyl-18,19,20-trinor-trans-4,5-didehydro-13,14-dihydro-6β-PGI₁, a prostacyclin analog according to claim 69.

71. A prostacyclin analog according to claim 68, wherein R₇ is

72. 2-Decarboxy-2-hydroxymethyl-15-phenoxy-17,18,19,20-tetranor-trans-4,5-didehydro-13,14-dihydro-6β-PGI₁, a prostacyclin analog according to claim 71.

73. A prostacyclin analog according to claim 68, wherein R₇ is —(CH₂)$_m$—CH₃—.

74. A prostacyclin analog according to claim 73, wherein R₅ is methyl.

75. 2-Decarboxy-2-hydroxymethyl-15-methyl-trans-4,5-didehydro-13,14-dihydro-6β-PGI₁, a prostacyclin analog according to claim 74.

76. A prostacyclin analog according to claim 73, wherein R₅ is hydrogen.

77. A prostacyclin analog according to claim 76, wherein at least one of R₃ and R₄ is fluoro.

78. 2-Decarboxy-2-hydroxymethyl-16,16-difluoro-trans-4,5-didehydro-13,14-dihydro-6β-PGI₁, a prostacyclin according to claim 77.

79. A prostacyclin analog according to claim 76, wherein at least one of R₃ and R₄ is methyl.

80. 2-Decarboxy-2-hydroxymethyl-16,16-dimethyl-trans-4,5-didehydro-13,14-dihydro-6β-PGI₁, a prostacyclin analog according to claim 79.

81. A prostacyclin analog according to claim 76, wherein R₃ and R₄ are both hydrogen.

82. 2-Decarboxy-2-hydroxymethyl-trans-4,5-didehydro-13,14-dihydro-6β-PGI₁, a prostacyclin analog according to claim 81.

* * * * *

UNITED STATES PATENT OFFICE
CERTIFICATE OF CORRECTION

Patent No. 4,200,740          Dated  29 April 1980

Inventor(s)  Donald E. Ayer

It is certified that error appears in the above-identified patent and that said Letters Patent are hereby corrected as shown below:

Column 6, line 42, "15-phenoxy-" should read -- 16-phenoxy- --.

Signed and Sealed this

Thirtieth Day of December 1980

[SEAL]

Attest:

SIDNEY A. DIAMOND

*Attesting Officer*     *Commissioner of Patents and Trademarks*